United States Patent
Xue et al.

(10) Patent No.: US 11,470,861 B2
(45) Date of Patent: Oct. 18, 2022

(54) PREPARATION METHOD AND APPLICATION OF ASTAXANTHIN H1-, OR H2- OR J-AGGREGATE WATER DISPERSION SYSTEM

(71) Applicant: OCEAN UNIVERSITY OF CHINA, Shandong (CN)

(72) Inventors: Changhu Xue, Shandong (CN); Jing Li, Shandong (CN); Mingqin Dai, Shandong (CN); Yaoguang Chang, Shandong (CN); Xingguo Liang, Shandong (CN); Jie Xu, Shandong (CN); Lu Yang, Shandong (CN)

(73) Assignee: OCEAN UNIVERSITY OF CHINA, Shandong (CN)

( * ) Notice: Subject to any disclaimer, the term of this patent is extended or adjusted under 35 U.S.C. 154(b) by 297 days.

(21) Appl. No.: 16/572,614

(22) Filed: Sep. 17, 2019

(65) Prior Publication Data
US 2020/0008446 A1  Jan. 9, 2020

(30) Foreign Application Priority Data
Feb. 1, 2019 (CN) .......................... 201910105838.X

(51) Int. Cl.
| | | |
|---|---|---|
| *A61K 31/122* | (2006.01) | |
| *A23K 20/179* | (2016.01) | |
| *A23L 5/42* | (2016.01) | |
| *A61K 47/26* | (2006.01) | |
| *A61K 47/36* | (2006.01) | |

(52) U.S. Cl.
CPC .............. *A23K 20/179* (2016.05); *A23L 5/42* (2016.08); *A61K 31/122* (2013.01); *A61K 47/26* (2013.01); *A61K 47/36* (2013.01)

(58) Field of Classification Search
None
See application file for complete search history.

(56) References Cited

FOREIGN PATENT DOCUMENTS

CN 105902401 A 8/2016

OTHER PUBLICATIONS

Machine Translation of CN105902401A retrieved from Espacenet on Aug. 20, 2021.*

Yingyuan Zhao, Junli Liu, Lei Guan, Yaping Zhang. Ping Dong, Jing Li, Xingguo Liang. Makoto Komiyama. Fabrication of aqueous nanodispersion from natural DNA and chitosan as eminent carriers for water-insoluble bioactives, International Journal of Biological Macromolecules, vol. 118, Part A, 2018, pp. 263-270, ISSN 0141-8130.

Marcel Fuciman, Milan Durchan, Václav Šlouf, Gürkan Keşan, Tomáš Polívka, Excited-state dynamics of astaxanthin aggregates. Chemical Physics Letters, vols. 568-569, 2013. pp. 21-25, ISSN 0009-2614.

Karki, Khadga & Samanta, Susruta & Roccatano, Danilo. (2016). Molecular Properties of Astaxanthin in Water/Ethanol Solutions from Computer Simulations. The journal of physical chemistry. B. 120. 10.1021/acs.jpcb.6b06055.

Liping Lu, Taoping Hu, Zhigang Xu, Structural characterization of astaxanthin aggregates as revealed by analysis and simulation of optical spectra. Spectrochimica Acta Part A: Molecular and Biomolecular Spectroscopy, vol. 185, 2017, pp. 85-92, ISSN 1386-1425.

Zajac, Grzegorz and Machalska, Ewa and Kaczor, Agnieszka and Kessler, Jiří and Bouř, Petr and Baranska, Malgorzata, Structure of supramolecular astaxanthin aggregates revealed by molecular dynamics and electronic circular dichroism spectroscopy, Phys. Chem. Chem. Phys., 2018, vol. 20. Issue 26, pp. 18038-18046, DOI 10.1039/C8CP01742E.

* cited by examiner

*Primary Examiner* — Jessica Worsham

(57) ABSTRACT

Preparation method and application of astaxanthin H1-, or H2- or J-aggregate water dispersion system are provided. The three kind of color-different astaxanthin multimer nanodispersion systems utilize a special molecular structure of natural biomacromolecule chitosan and fish sperm DNA as well as physical interaction between macromolecules to induce formation and stability of astaxanthin multimers under solvent and salt ion-effects. Low-toxicity ethanol is selected as a good solvent for astaxanthin. The organic solvent can be completely removed in the later stage of the preparation process, and can be further enriched and recycled, which is beneficial to clean production and low cost. By adjusting process parameters, the H1-, or H2- or J-type astaxanthin aggregate water dispersion system can be obtained, so as to control a coloration range of astaxanthin water-based products to be yellow, orange and pink. Furthermore, during concentration, dehydration and reconstitution, astaxanthin aggregation patterns and coloring effects are maintained.

7 Claims, 3 Drawing Sheets

PREPARATION METHOD AND APPLICATION OF ASTAXANTHIN H1-, OR H2- OR J-AGGREGATE WATER DISPERSION SYSTEM

CROSS REFERENCE OF RELATED APPLICATION

The present invention claims priority under 35 U.S.C. 119(a-d) to CN 201910105838.X, filed Feb. 1, 2019.

BACKGROUND OF THE PRESENT INVENTION

Field of Invention

The present invention relates to water-dispersible system containing stable multimers of astaxanthin in a certain aggregation form, and more particularly to an H1-, or H2- or J-type astaxanthin aggregate water dispersion system presented as an astaxanthin H1-, or H2- or J-aggregate with a controllable manner of the aggregation form, belonging to technical fields of food, medicine and chemical industry.

Description of Related Arts

Astaxanthin is widely found in nature, such as in flowers, leaves, fruits, crustaceans, fishes, algae, and the like. As a fat-soluble pigment, astaxanthin is widely used in aquaculture, daily chemical and medical health industries because of its bright color and strong antioxidant activity. Among them, natural astaxanthin derived from haematococcus pluvialis is the strongest antioxidant found in nature and the only carotenoid that can pass the blood-brain barrier, so it can be used as a dietary supplement, food additive, coloring agents, antioxidants, etc.

Due to excellent coloring power of astaxanthin and the absorption spectrum shift induced by astaxanthin aggregation, crustaceans and birds with rich astaxanthin in biological tissues can exhibit different colors. For example, astaxanthin is the only color component of the crustacyanin in the lobster shell. After astaxanthin binds to the crustacyanin, the absorption spectrum of astaxanthin is significantly red-shifted, this may be related to molecular aggregation that occurs during the interaction between astaxanthin and crustacyanin. In vitro studies have shown that hydrophobic astaxanthin monomer molecules can undergo molecular aggregation in aqueous organic solvent systems, resulting in two distinctly different aggregates. One is an H-type astaxanthin aggregate formed by stacking astaxanthin monomer molecules in a "face-to-face" parallel conjugated chain, and its maximum absorption wavelength is blue-shifted relative to the maximum absorption wavelength of astaxanthin free monomer. The other is a J-type astaxanthin aggregate consisting of loose astaxanthin monomer molecules in a "head-to-tail" dislocation parallel stack, and its maximum absorption wavelength is red-shifted relative to the maximum absorption wavelength of astaxanthin free monomer. Fuciman et al. (2013) further found that astaxanthin dissolved in hydrated DMSO solution can form two kinds of H-type astaxanthin aggregates, namely H1-type and H2-type astaxanthin aggregate, respectively, and the maximum absorption peak of each type aggregate solution exhibited varying degrees of blue shift. The maximum absorption peak of H1-type astaxanthin aggregate is blue-shifted to 386 nm relative to the absorption peak of free astaxanthin monomer (504 nm), and is closely stacked and parallel arranged by a large number of astaxanthin monomer molecules in a "face-to-face" manner, thus having a narrower absorption peak. H2-type astaxanthin aggregate is a very unstable, transiently aggregated form, which is loosely stacked and parallel arranged by astaxanthin monomer molecules in a "face-to-face" manner, wherein its maximum absorption peak is blue-shifted to 460 nm relative to the absorption peak of free astaxanthin monomer (504 nm), and its maximum absorption peak is wider. Lu et al. (2017) used linear spectroscopy and Frenkel exciton models to simulate the aggregation and spectral changes of astaxanthin in a blend of ethanol and water. The calculations showed that the sharp absorption peak exhibited by H-type aggregate at 387 nm is induced by a large amount of astaxanthin hexamer, that is, H1-type aggregate. Meanwhile, when the astaxanthin molecular composition is sparse, that is, mainly represented by monomers, dimers, and trimers, a broad peak will appear at 400-500 nm, that is, an H2-type aggregate. In fact, in a simple aqueous solution of ethanol, the sparsely stacked H2-type astaxanthin aggregate and the closely stacked H1-type astaxanthin aggregate are dynamically converting processes and cannot be separated as well as maintained their stable aggregation status. Conventionally, there is no report on the use of the same biomolecular materials to control the water dispersion system of H1-, or H2- or J-type astaxanthin aggregate with different colors by controlling the preparation parameters only. The acquisition of astaxanthin aggregate with different spectral properties and microstructures is of great significance for scientific research such as the structure-effect relationship of astaxanthin and for the application of astaxanthin functional products and astaxanthin multicolor coloration.

SUMMARY OF THE PRESENT INVENTION

An object of the present invention is to solve problems that astaxanthin is hardly soluble in water and color of the solution is single, free astaxanthin is unstable, and a microstructure of water-dispersed astaxanthin is uncontrollable, wherein chitosan, natural DNA and salt solution are utilized to construct stable microenvironment for astaxanthin aggregation, thereby providing a preparation method of an H1-, or H2- or J-type astaxanthin aggregate water dispersion system with three different colors.

The H1- or H2- or J-type astaxanthin aggregate water dispersion system of the present invention comprises water, an inorganic salt, and composite particles comprising astaxanthin aggregates; the inorganic salt is a sodium salt or a potassium salt;

wherein the composite particles comprising the astaxanthin aggregate are formed by chitosan, natural DNA and astaxanthin, wherein the astaxanthin is stably embedded in a hydrophobic microdomains formed by intercalation of chitosan and DNA molecules in a certain aggregate type; an average particle size of the composite particles is less than 1 μm, surfaces of the composite particles have a large amount of positive charges, and a zeta potential is greater than 20 mV; the composite particles are stably dispersed in water, and the system has high transparency as light transmittance is over 90%.

Since the system is a hydrophilic system, and main components are the astaxanthin, the chitosan, the natural DNA and a small amount of inorganic salts without other chemical synthetic substances such as oil agents and surfactants, biosafety, biocompatibility and biodegradability are sufficient.

A preparation method of an H1-type astaxanthin aggregate water dispersion system is provided, comprising steps of:

1) dissolving astaxanthin in any volume of ethanol at 4-25° C. in dark, so as to obtain an astaxanthin ethanol solution, the used ethanol should have a volume fraction greater than 95%; if there is undissolved astaxanthin, removing undissolved astaxanthin particles by centrifugation or filtration;

2) dissolving solid DNA in water at a room temperature, and autoclaving at 120° C. for 30 min to obtain a DNA solution of 0.01-0.5 mg/ml;

3) dissolving chitosan in a hydrochloric acid solution or an acetic acid solution of pH 1-4 at the room temperature, then adjusting the pH to 5-6 with a sodium hydroxide solution or a potassium hydroxide solution to obtain a chitosan solution with a chitosan content of 0.01-0.5 mg/ml;

4) rapidly adding the astaxanthin ethanol solution prepared in the step 1) to the chitosan solution prepared in the step 3) at 20-25° C.; controlling a volume ratio of an ethanol phase and an aqueous phase within a range of 1:5-1:10, and stirring at 200-500 rpm for more than 30 minutes;

wherein a stirring time is more than 30 min for forming stable astaxanthin H1-aggregate, stirring time less than 30 min cannot form stable aggregates;

5) slowly adding the DNA solution prepared in the step 2) to a mixture prepared in the step 4) while stirring at 200-500 rpm, and controlling a volume ratio of the DNA solution and the aqueous phase of the step 4) at 1:2; keeping stirring at 20-25° C. for 15-20 min;

6) removing an ethanol solvent under 25-35° C. and a vacuum pressure of 2-8 mbar by suspending and evaporating, in such a manner that an ethanol residual amount in the system is less than 1%; and 7) adding oligo-chitosan to the ethanol-removed system at the room temperature to adjust a final concentration of the oligo-chitosan at 0.001-0.2 wt %, and thoroughly mixing to obtain an water-dispersible astaxanthin H1-aggregate nano-dispersion system, i.e., H1-type astaxanthin aggregate water dispersion system.

In the step 1), a centrifugation speed is 10000 rpm and a centrifugation time is 5-15 min;

In the step 1), filtration uses a microporous membrane (for example, with a pore size below 0.8 μm);

In the step 4), rapidly adding is pouring or adding with a flow rate of more than 20 cm$^3$/s;

In the step 5), slowly adding is adding with a flow rate of 0.02-2 cm$^3$/s.

The H1-type astaxanthin aggregate water dispersion system is a colloid having a particle size of 50-300 nm and light transmittance of greater than 90%. The astaxanthin molecules in the system are connected in a head-to-head and tail-to-tail form, so as to be closely stacked into an astaxanthin H1-aggregate. The aggregate exhibits a transparent yellow color in water and maximum light absorption at a wavelength of 380 to 390 nm. It should be noted that in the above method, the concentration of the astaxanthin ethanol solution can be any concentration, that is, the unsaturated solution of the astaxanthin can also be used to prepare a dispersion system having a transparent yellow color, which is far superior to the conventional method where a saturated astaxanthin ethanol solution must be used.

A preparation method of an H2-type astaxanthin aggregate water dispersion system is also provided, comprising steps of:

1) dissolving astaxanthin in any volume of ethanol at 4-25° C. in dark, so as to obtain an astaxanthin ethanol solution, the used ethanol should have a volume fraction greater than 95%; if there is undissolved astaxanthin, removing undissolved astaxanthin particles by centrifugation or filtration;

2) dissolving solid DNA in water at a room temperature, and autoclaving at 120° C. for 30 min to obtain a DNA solution of 0.01-0.5 mg/ml;

3) dissolving chitosan in a hydrochloric acid solution or an acetic acid solution of pH 1-4 at the room temperature, then adjusting the pH to 5-6 with a sodium hydroxide solution or a potassium hydroxide solution; then adding sodium chloride to the solution and fully dissolving and mixing to adjust a final concentration of the sodium chloride to 3.5-35 mg/ml, so as to obtain a chitosan solution with a chitosan content of 0.01-0.5 mg/ml;

4) rapidly adding the astaxanthin ethanol solution prepared in the step 1) to the chitosan solution prepared in the step 3) at 20-25° C.; controlling a volume ratio of an ethanol phase and an aqueous phase within a range of 1:5-1:10, and stirring at 1000-2000 rpm for 3 minutes;

wherein when the astaxanthin is poured in, a stirring speed is instantly increased to 1000-2000 rpm, and a stirring time is shorten to 3 minutes;

5) slowly adding the DNA solution prepared in the step 2) to a mixture prepared in the step 4) while stirring at 200-500 rpm, and controlling a volume ratio of the DNA solution and the aqueous phase of the step 4) at 1:2; keeping stirring at 20-25° C. for 15-20 min;

6) removing an ethanol solvent under 25-35° C. and a vacuum pressure of 2-8 mbar by suspending and evaporating, in such a manner that an ethanol residual amount in the system is less than 1%; and 7) adding oligo-chitosan to the ethanol-removed system at the room temperature to adjust a final concentration of the oligo-chitosan at 0.001-0.2 wt %, and thoroughly mixing to obtain an H2-type astaxanthin aggregate water dispersion system.

In the step 1), a centrifugation speed is 10000 rpm and a centrifugation time is 5-15 min;

In the step 1), filtration uses a microporous membrane (for example, with a pore size below 0.8 μm);

In the step 4), rapidly adding is pouring or adding with a flow rate of more than 20 cm$^3$/s;

In the step 5), slowly adding is adding with a flow rate of 0.02-2 cm$^3$/s.

The H2-type astaxanthin aggregate water dispersion system is a colloid having a particle size of 200-600 nm and light transmittance of greater than 90%. The astaxanthin molecules in the system are connected in a head-to-head and tail-to-tail form, so as to be loosely stacked into an astaxanthin H2-aggregate. The aggregate exhibits a transparent orange color in water and maximum light absorption at a wavelength of 457 to 467 nm.

A preparation method of a J-type astaxanthin aggregate water dispersion system is also provided, comprising steps of:

1) dissolving astaxanthin in any volume of ethanol at 4-25° C. in dark, so as to obtain an astaxanthin ethanol solution, the used ethanol should have a volume fraction greater than 95%; if there is undissolved astaxanthin, removing undissolved astaxanthin particles by centrifugation or filtration;

2) dissolving solid DNA in water at a room temperature, and autoclaving at 120° C. for 30 min to obtain a DNA solution of 0.01-0.5 mg/ml;

3) dissolving chitosan in a hydrochloric acid solution or an acetic acid solution of pH 1-4 at the room temperature, then adjusting the pH to 5-6 with a sodium hydroxide solution or a potassium hydroxide solution to obtain a chitosan solution with a chitosan content of 0.01-0.5 mg/ml;

4) rapidly adding the astaxanthin ethanol solution prepared in the step 1) to the chitosan solution prepared in the step 3) at 20-25° C.; controlling a volume ratio of an ethanol phase and an aqueous phase within a range of 1:2-1:10, and stirring at 200-500 rpm for 15-30 minutes; wherein the astaxanthin ethanol solution is freshly dissolved and stored form no more than 2 days;

5) slowly adding the DNA solution prepared in the step 2) to a mixture prepared. in the step 4) while stirring at 200-500 rpm, and controlling a volume ratio of the DNA solution and the aqueous phase of the step 4) at 1:2; keeping stirring at 20-25° C. for 15-20 min;

6) removing an ethanol solvent under 25-35° C. and a vacuum pressure of 2-8 mbar by suspending and evaporating, in such a manner that an ethanol residual amount in the system is less than 1%; and 7) adding oligo-chitosan to the ethanol-removed system at the room temperature to adjust a final concentration of the oligo-chitosan at 0.001-0.2 wt %, and thoroughly mixing to obtain a J-type astaxanthin aggregate water dispersion system.

The J-type astaxanthin aggregate water dispersion system is a colloid having a particle size of 200-800 nm and light transmittance of greater than 90%. The astaxanthin molecules in the system are connected in a head-to-tail form, so as to be stacked into an astaxanthin J-aggregate. The aggregate exhibits a transparent pink color in water and two side-to-shoulder peaks at wavelengths 525 nm and 565 nm. It should be noted that in the above method, the concentration of the astaxanthin ethanol solution can be any concentration, that is, the unsaturated solution of the astaxanthin can also be used to prepare a dispersion system having a transparent pink color, which is far superior to the conventional method where a saturated astaxanthin ethanol solution must be used.

Preferably, processing parameters of the above preparation methods are as follows:

in the step 1), a centrifugation speed is 10000 rpm and a centrifugation time is 5-15 min;

in the step 1), filtration uses a microporous membrane (for example, with a pore size below 0.8 μm);

in the step 4), rapidly adding is pouring or adding with a flow rate of more than 20 cm$^3$/s;

in the step 5), slowly adding is adding with a flow rate of 0.02-2 cm$^3$/s.

Preferably, raw materials in the above preparation methods are as follows:

in the step 1), the astaxanthin is one of a 3S-3'S configuration, a 3R-3'R configuration and a 3R-3'S configuration;

in the step 3), the chitosan has a deacetylation degree ranging from 72-99% and a molecular weight ranging from 50-150 kDa;

in the step 7), the oligo-chitosan is water-soluble chitosan having a deacetylation degree of more than 90% and a molecular weight ranging from 1-8 kDa;

in the step 2), the solid DNA used is long-chain, linear DNA with a double helix structure, which is natural DNA with a molecular weight of more than 10 Kbp extracted from animals, plants or microbial tissues, for example, salmon sperm DNA.

Products prepared by the above preparation methods can be used as follows:

The H1-, or H2- or J-type astaxanthin aggregate water dispersion system can be used by: using the prepared nano-dispersion system as a food coloring agent, a meal, a health care product, a daily chemical product, and a feed;

The H1-, or H2- or J-type astaxanthin aggregate water dispersion system can be used by: drying and dehydrating the nano-dispersion system to obtain solid powder, or concentrating to obtain a colloid having a high astaxanthin content; and directly adding the solid powder or the colloid to an aqueous base, an emulsion or a solid material and mixing, or encapsulating in a soft or hard capsule shell; and then processing into a food colorant, a special diet, a health care product, a daily chemical product, or a feed.

The aqueous base comprises mineral water, purified water and distilled water; the emulsion comprises milk, fermented milk, and emulsifier; and the solid material comprises starch, dextrin, microcrystalline cellulose, and gelatin.

Beneficial Effects

The preparation method of water-dispersible astaxanthin multimer nano-dispersion system is simple and easy, and the preparation process has no special conditions such as high temperature and high pressure. The operation and control are relatively simple, and the production can be continuously performed. The solvent residue in the product is low, and the organic solvent ethanol can be removed and recycled, which is conducive to clean green production, low production costs, and high bioavailability of products. Ethanol is selected as a good solvent with low toxicity to dissolve astaxanthin, and there is no need to add high-toxic organic solvents such as acetone, ethyl acetate and chloroform, which is suitable as a preparation method of food grade astaxanthin product. The key of this method is to control the orderly accumulation of astaxanthin molecules by controlling the feeding sequence, the feed ratio, and the salt solution. The added natural DNA and chitosan stabilize the astaxanthin multimer structure while encapsulates the astaxanthin multimer, and the further solvent evaporation process promotes the formation of H1-, or H2- or J-type aggregation form of astaxanthin multimer. Finally, the oligo-chitosan is added to maintain the stability of the colloidal system and the positive charge of the surface of the composite particles, which is beneficial to absorption. Moreover, the entire preparation method is not critical to the conditions such as the concentration of the raw materials, and it is only necessary to control the results of each step as in steps 3 and 4 to achieve the final effect. Conventional methods use saturated astaxanthin ethanol solution for similar preparation, which have obvious disadvantage that filtration or the like must be adopted when obtaining a saturated solution, which is bound to cause waste of astaxanthin and complicated process.

The material used in the method is natural, safe and non-toxic, and the prepared astaxanthin multimer nano-dispersion system is a colloid which can be dispersed in the water phase with high transparency, wherein light transmittance is over 90%, and ethanol residue amount is <1%, providing good biosafety, biocompatibility and biodegradability. The average particle size of the uniformly dispersed composite particles in the system is less than 1 μm, showing small sizes, large surface areas and high surface energy, which is beneficial to absorption and utilization by body. The astaxanthin multimer immobilized inside the composite particles exists in three different aggregation states of H1-type, H2-type and J-type instead of astaxanthin monomer. Therefore, the three kinds of astaxanthin multimer nano-dispersion systems present three distinct colors, wherein the H1-type astaxanthin aggregate water dispersion system is yellow with maximum light absorption in the wavelength range of 380-390 nm; and the H2-type astaxanthin aggregate water dispersion system is orange with maximum light absorption in the wavelength range of 457-467 nm; and the J-type astaxanthin aggregate water dispersion system is pink with maximum light absorption in the wavelength range of 525-565 nm. The three kinds of astaxanthin multimer nano-dispersion systems can be miscible, diluted, concentrated or lyophilized with water in any ratio without changing the molecular aggregation state of astaxanthin, and have more stability and controllability than ever before. They are suitable for further processing into food colorants, special diets, health care products, daily chemical products, and feeds.

The astaxanthin in the composite particles is stably presented in the hydrophobic microdomains of the particles in a specific aggregation form, which can improve the stability of astaxanthin during storage, transportation, digestion and absorption in the body, and can also improve dispersibility of astaxanthin in water.

The present invention utilizes the same biomacromolecules, and can obtain three color-different H1-, or H2- or J-type astaxanthin aggregate water dispersion system by adding characteristic salt solution and controlling reaction conditions, which breaks through that only one stable astaxanthin micro/nano suspension can be obtained when a specific wall material and a specific astaxanthin micro/nano preparation technique are utilized.

DETAILED DESCRIPTION OF THE PREFERRED EMBODIMENT

Figure 1:
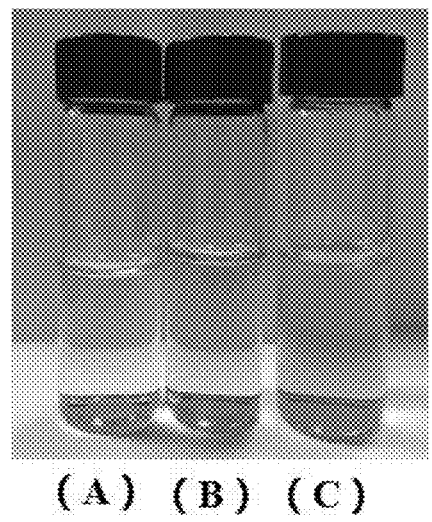
FIG. 1 illustrates a yellow H1-type astaxanthin aggregate water dispersion system (A), an orange H2-type astaxanthin aggregate water dispersion system (B) and a pink J-type astaxanthin aggregate water dispersion system (C) which are freshly prepared.

Embodiment 1: Preparation of a Yellow H1-Type Astaxanthin Aggregate Water Dispersion System Taking a 1000 mL eggplant bottle, placing a rotor in the eggplant bottle and fixing on a magnetic stirrer, and setting a rotation speed to 300 rpm; in dark and argon protection, adding 30 mL 10 µg/mL astaxanthin ethanol solution and 160 mL 0.02 mg/ml chitosan (deacetylation degree 90.3%, molecular weight 80 kD) solution to the eggplant bottle in sequence, and magnetically stirring for 30 min; then adding 80 mL 0.02 mg/mL salmon sperm DNA solution to the mixed system within 10 min, and magnetically stirring for 15 min; turning on a rotary evaporator and setting a condensing temperature to −15° C., a water bath temperature to 25° C. and a rotation speed to 50 rpm; processing the mixed reaction system with rotary evaporation under 8 mbar to remove ethanol, and then adding an equal volume of 1% oligo-chitosan (deacetylation degree 92%, molecular weight 5 kD) to obtain the yellow H1-type astaxanthin aggregate water dispersion system.

Embodiment 2: Preparation of an Orange H2-Type Astaxanthin Aggregate Water Dispersion System Taking a 1000 mL eggplant bottle, placing a rotor in the eggplant bottle and fixing on a magnetic stirrer, and setting a rotation speed to 300 rpm; adding 160 mL 0.02 mg/ml chitosan (deacetylation degree 90.3%, molecular weight 80 kD) solution and a sodium chloride solution with a final concentration of 5 mg/mL to the eggplant bottle in sequence; thoroughly stirring and adding 30 mL 0.01 mg/mL astaxanthin ethanol solution which has been dissolved and allowed to stand for 3 days, and magnetically stir for 3 min; then adding 80 mL 0.02 mg/mL salmon sperm DNA solution to the mixed system within 10 min, and magnetically stirring for 15 min; turning on a rotary evaporator and setting a condensing temperature to −15° C., a water bath temperature to 25° C. and a rotation speed to 50 rpm; processing the mixed reaction system with rotary evaporation under 8 mbar to remove ethanol in dark, so as to obtain the orange H2-type astaxanthin aggregate water dispersion system.

Embodiment 3: Preparation of a Pink J-Type Astaxanthin Aggregate Water Dispersion System Taking a 1000 mL eggplant bottle, placing a rotor in the eggplant bottle and fixing on a magnetic stirrer, and setting a rotation speed to 300 rpm; adding 80 mL astaxanthin ethanol solution (0.007 mg/mL) which has been dissolved and allowed to stand for 12 h and 160 mL 0.02 mg/mL chitosan (deacetylation degree 90.3%, molecular weight 80 kD) solution to the eggplant bottle in sequence, and magnetically stirring for 30 min; then adding 80 mL 0.02 mg/mL salmon sperm DNA solution to the mixed system within 10 min, and magnetically stirring for 15 min; turning on a rotary evaporator and setting a condensing temperature to −15° C., a water bath temperature to 25° C. and a rotation speed to 50 rpm; processing the mixed reaction system with rotary evaporation under 8 mbar to remove ethanol, and then adding an equal volume of 1% oligo-chitosan (deacetylation degree 92%, molecular weight 5 kD) to obtain the pink J-type astaxanthin aggregate water dispersion system.

Embodiment 4: Color Observation and Astaxanthin Detection of Astaxanthin Multimer Nano-Dispersion Systems 1) Color observation: colors of freshly prepared two types of astaxanthin H-aggregates water dispersion systems are compared and photographed for observing. Referring to FIG. 1, the H1-type astaxanthin aggregate water dispersion system is yellow (FIG. 1A), the H2-type astaxanthin aggregate water dispersion system is orange (FIG. 1B), and the J-type astaxanthin aggregate water dispersion system is pink (FIG. 1C), the three kinds of astaxanthin multimer nano-dispersion systems have high transparency and clarity.

Figure 2:
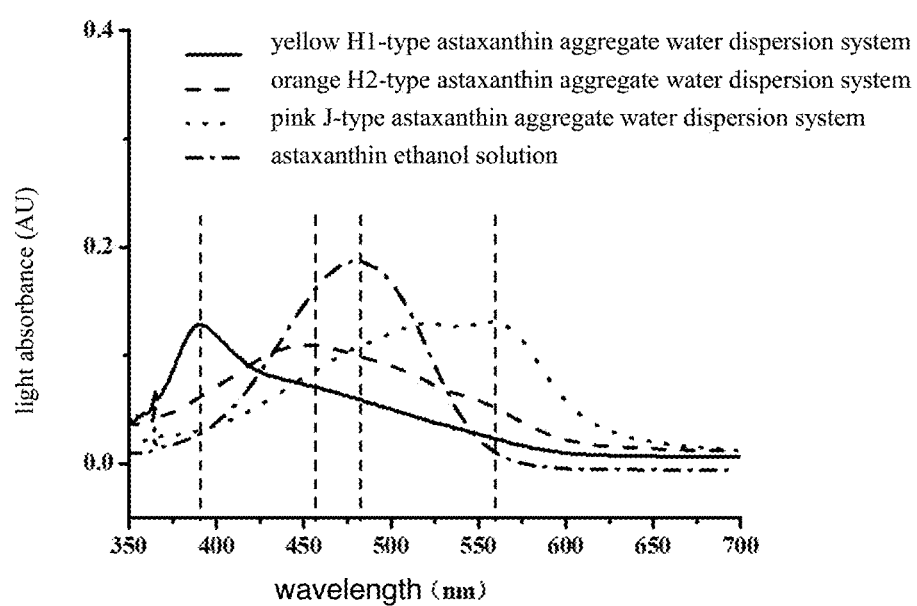
FIG. 2 is a UV-Vis spectrum of the three types of astaxanthin aggregate water dispersion systems of FIG. 1.

2) Ultraviolet-visible spectroscopic spectrum: the three kinds of astaxanthin multimer nano-dispersion systems and astaxanthin ethanol solutions prepared in the embodiments 1, 2, and 3 were subjected to full-wavelength scanning using an ultraviolet-visible spectrophotometer. It can be seen from the scanning spectrum of FIG. 2 that the formed three kinds of water dispersion systems have different absorption spectrum curves, wherein the yellow astaxanthin H1-aggregate water dispersion system has maximum light absorption at a wavelength of 380 nm, and a peak shape is narrow, indicating that astaxanthin molecules are relatively closely arranged; the orange astaxanthin H2-aggregate water dispersion system has maximum light absorption at a wavelength of 457 nm, and a peak shape is wide, indicating that the astaxanthin molecules are relatively loosely arranged; the pink astaxanthin J-aggregate water dispersion system has two side-to-shoulder peaks at wavelengths of 525 and 565 nm, and a peak shape is wide, indicating that the astaxanthin molecules are relatively loosely arranged. The maximum absorption peaks of the three kinds of astaxanthin multimer nano-dispersion systems are different from a maximum absorption wavelength of free astaxanthin (480 nm), indicating that astaxanthin multimer nano-dispersion systems with three different aggregation patterns were obtained.

Figure 3:
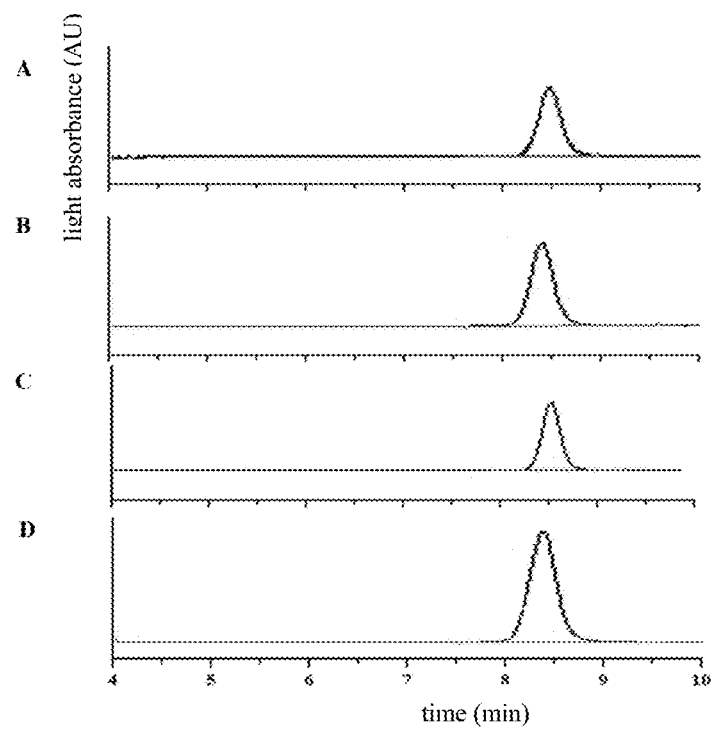
FIG. 3 is HPLC test results of astaxanthin in the three types of astaxanthin aggregate water dispersion systems in FIG. 1 and an astaxanthin ethanol solution, wherein A is the H1-type astaxanthin aggregate water dispersion system, B is the H2-type astaxanthin aggregate water dispersion system, C is the J-type astaxanthin aggregate water dispersion system, and D is the astaxanthin ethanol solution.

3) Determination of astaxanthin in the astaxanthin multimer nano-dispersion systems by HPLC: liquid phase conditions are: chromatography column is China Dalian Elite YLT-OBS (4.6 mm*200 mm, 5 μm); mobile phase is 85% methanol, 5% dichloromethane, 5% water and 5% acetonitrile; gradient elution is used; flow rate is 1.0 mL/min; measurement wavelength is 480 nm; injection volume 10 μL. An extraction method of astaxanthin in the yellow H1-type astaxanthin aggregate water dispersion system, the orange H2-type astaxanthin aggregate water dispersion system and the pink J-type astaxanthin aggregate water dispersion system is: adding 3 mL of fresh nano-suspension into an extraction bottle, adding 2 mL of dichloromethane and methanol, and placing extracted lower layer liquid in an eggplant type bottle; adding 2 mL dichloromethane to upper layer liquid for repeatedly extracting until the upper layer liquid became clear; processing the organic solvent in the eggplant bottle with evaporation before reconstituting the astaxanthin in the eggplant bottle with a mobile phase, and passing through a 0.22 μm organic phase filter for sample testing; meanwhile, taking 1.5 mL astaxanthin ethanol solution and passing through a 0.22 μm organic phase filter for sample testing. It can be judged from peak times of FIG. 3 that the substances extracted from the three multimer nano-dispersion systems are astaxanthin, indicating that astaxanthin is stably present in the astaxanthin colloidal systems, and molecular aggregation states are maintained in initial stages of preparation. It can also be seen that the present invention is very effective in obtaining dispersion systems of different colors by adjusting the aggregation states of free molecules of astaxanthin.

Figure 4:
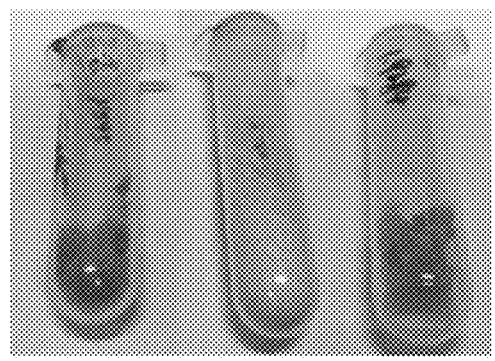
FIG. 4 is a photograph of lyophilized solid samples of the three types of astaxanthin aggregate water dispersion systems of FIG. 1, wherein A is the lyophilized solid sample of the H1-type astaxanthin aggregate water dispersion system, B is the lyophilized solid sample of the H2-type astaxanthin aggregate water dispersion system, and C is the lyophilized solid sample of the J-type astaxanthin aggregate water dispersion system.
Figure 5:
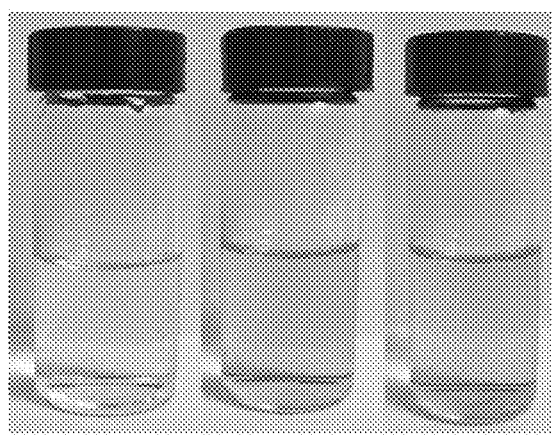
FIG. 5 is a photograph of the solid samples of the three types of astaxanthin aggregate powder of FIG. 4 after reconstitution in water, wherein A is a reconstituted sample of the yellow H1-type, B is a reconstituted sample of the orange H2-type, and C is a reconstituted sample of the pink J-type.

Embodiment 5: Application of Astaxanthin Multimer Nano-Dispersion Systems of the Present Invention Pouring the three kinds of astaxanthin multimer nano-dispersion systems of the embodiments 1, 2 and 3 respectively into a freezer tray, wherein a liquid level does not exceed 2 cm, and then placing the freezing tray in a −80° C. refrigerator for 12 h; turning on a vacuum freeze dryer for pre-cooling at −50° C. for 30 min, and placing the freezing tray in a lyophilizer for 24 h before removing the freezing tray; quickly transferring nano-lyophilized powder in the freezing tray to a glass container to seal, protect from light, store at −80° C. to −20° C.; before reconstitution, restoring the nano-lyophilized powder to a room temperature, and then adding an appropriate amount of the nano-lyophilized powder to pure water to dissolve, thereby obtaining an astaxanthin multimer reconstitution solution. It can be seen from FIG. 4 and FIG. 5 that the colors of the three kinds of astaxanthin multimer nano-dispersion systems after lyophilization and reconstitution still stay the same as the color of the fresh samples (as shown in FIG. 1) The results indicate that the astaxanthin multimer nano-dispersion systems can be further used for the production of other dosage forms by freeze-drying into solid preparations, and can also be effectively concentrated by lyophilization and reconstitution.

What is claimed is:

1. A preparation method of an H2-type astaxanthin aggregate water dispersion system, comprising steps of:
   1) dissolving astaxanthin in any volume of ethanol at 4-25° C. in dark, so as to obtain an astaxanthin ethanol solution, wherein the ethanol has a volume fraction greater than 95%; if there is undissolved astaxanthin, removing undissolved astaxanthin particles by centrifugation or filtration;
   2) dissolving solid DNA in water at room temperature, and autoclaving at 120° C. for 30 min to obtain a DNA solution of 0.01-0.5 mg/ml;
   3) dissolving chitosan in a hydrochloric acid solution or an acetic acid solution of pH 1-4 at room temperature, then adjusting the pH to 5-6 with a sodium hydroxide solution or a potassium hydroxide solution; then adding sodium chloride to the solution and fully dissolving and mixing to adjust a final concentration of the sodium chloride to 3.5-35 mg/ml, so as to obtain a chitosan solution with a chitosan content of 0.01-0.5 mg/ml;
   4) rapidly adding the astaxanthin ethanol solution prepared in the step 1) to the chitosan solution prepared in the step 3) at 20-25° C.; controlling a volume ratio of an ethanol phase and an aqueous phase within a range of 1:5-1:10, and stirring at 1000-2000 rpm for 3 minutes;
   5) slowly adding the DNA solution prepared in the step 2) to a mixture prepared in the step 4) while stirring at 200-500 rpm, and controlling a volume ratio of the DNA solution and the aqueous phase of the step 4) at 1:2; keeping stirring at 20-25° C. for 15-20 min;
   6) removing an ethanol solvent under 25-35° C. and a vacuum pressure of 2-8 mbar by suspending and evaporating, in such a manner that an ethanol residual amount in the system is less than 1%; and
   7) adding oligo-chitosan to the ethanol-removed system at room temperature to adjust a final concentration of the oligo-chitosan at 0.001-0.2 wt %, and thoroughly mixing to obtain an H2-type astaxanthin aggregate water dispersion system.

2. The preparation method, as recited in claim 1, wherein:
   in the step 1), a centrifugation speed is 10000 rpm and a centrifugation time is 5-15 min;
   in the step 1), filtration uses a microporous membrane with a pore size below 0.8 μm;
   in the step 4), rapidly adding is pouring or adding with a flow rate of more than 20 cm$^3$/s; and in the step 5), slowly adding is adding with a flow rate of 0.02-2 cm³/s.

3. The preparation method, as recited in claim 1, wherein in the step 1), the astaxanthin is one of a 3S-3'S configuration, a 3R-3'R configuration and a 3R-3'S configuration.

4. The preparation method, as recited in claim 1, wherein:
in the step 3), the chitosan has a deacetylation degree ranging from 72-99% and a molecular weight ranging from 50-150 kDa; and
in the step 7), the oligo-chitosan is water-soluble chitosan having a deacetylation degree of more than 90% and a molecular weight ranging from 1-8 kDa.

5. The preparation method, as recited in claim 1, further comprising a step of: using the prepared astaxanthin aggregate water dispersion system as a food coloring agent, a meal, a health care product, a daily chemical product, and a feed.

6. The preparation method, as recited in claim 1, further comprising steps of: drying and dehydrating the H2-type astaxanthin aggregate water dispersion system to obtain solid powder, or concentrating to obtain a colloid having a high astaxanthin content; and directly adding the solid powder or the colloid to an aqueous base, an emulsion or a solid material and mixing, or encapsulating in a soft or hard capsule shell; and then processing into a food colorant, a special diet, a health care product, a daily chemical product, or a feed.

7. The preparation method, as recited in claim 1, wherein in the step 2), the solid DNA used is long-chain, linear DNA with a double helix structure, which is salmon sperm DNA with a molecular weight of more than 10 KB.

\* \* \* \* \*